United States Patent
Choi et al.

(10) Patent No.: US 10,292,682 B2
(45) Date of Patent: May 21, 2019

(54) METHOD AND MEDICAL IMAGING APPARATUS FOR GENERATING ELASTIC IMAGE BY USING CURVED ARRAY PROBE

(71) Applicant: SAMSUNG ELECTRONICS CO., LTD., Suwon-si (KR)

(72) Inventors: Ki-wan Choi, Seoul (KR); Jun-ho Park, Hwaseong-si (KR); Hyoung-ki Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 202 days.

(21) Appl. No.: 14/714,579

(22) Filed: May 18, 2015

(65) Prior Publication Data
US 2016/0089113 A1    Mar. 31, 2016

Related U.S. Application Data

(63) Continuation of application No. PCT/KR2014/012781, filed on Dec. 24, 2014.

(30) Foreign Application Priority Data

Sep. 29, 2014   (KR) .................. 10-2014-0130328

(51) Int. Cl.
*A61B 8/08*     (2006.01)
*G01S 15/89*    (2006.01)
(Continued)

(52) U.S. Cl.
CPC .......... *A61B 8/485* (2013.01); *G01S 7/52022* (2013.01); *G01S 7/52042* (2013.01);
(Continued)

(58) Field of Classification Search
CPC .................................................... A61B 8/485
See application file for complete search history.

(56) References Cited

U.S. PATENT DOCUMENTS 5,103,129 A * 4/1992 Slayton ................. B06B 1/0622
310/334
6,193,659 B1 * 2/2001 Ramamurthy ......... A61B 8/481
600/443
(Continued)

FOREIGN PATENT DOCUMENTS

JP        2008-264540 A       11/2008
KR      10-0748585 B1          8/2007
(Continued)

OTHER PUBLICATIONS

Communication dated Nov. 16, 2015, issued by the Korean Intellectual Property Office in counterpart Korean Patent Application No. 10-2014-0130328.
(Continued)

*Primary Examiner* — Rochelle D Turchen
(74) *Attorney, Agent, or Firm* — Sughrue Mion, PLLC

(57) ABSTRACT

A method of generating an ultrasound elastic image includes: inducing a shear wave that propagates in a second direction by transmitting a first ultrasound signal including a push signal to an object in a first direction, by a curved array probe; transmitting a second ultrasound signal to the object and receiving an echo signal reflected by the object in response to the second ultrasound signal, via the curved array probe; and generating an elastic image of the object by using the received echo signal. The second ultrasound signal includes a plane wave having a straight line waveform parallel to the second direction.

20 Claims, 20 Drawing Sheets

(51) Int. Cl.
*G01S 7/52* (2006.01)
*A61B 8/00* (2006.01)

(52) U.S. Cl.
CPC ........... *G01S 15/892* (2013.01); *A61B 8/4488* (2013.01); *A61B 8/5207* (2013.01)

(56) References Cited

U.S. PATENT DOCUMENTS

| | | | | |
|---|---|---|---|---|
| 6,503,201 | B1* | 1/2003 | Liu | G01S 7/52046 600/443 |
| 6,770,033 | B1 | 8/2004 | Fink et al. | |
| 7,252,004 | B2 | 8/2007 | Fink et al. | |
| 2006/0241459 | A1* | 10/2006 | Tai | A61B 8/06 600/454 |
| 2007/0016066 | A1 | 1/2007 | Lee et al. | |
| 2008/0097206 | A1* | 4/2008 | Chomas | A61B 8/481 600/439 |
| 2008/0255456 | A1 | 10/2008 | Kye et al. | |
| 2009/0216119 | A1 | 8/2009 | Fan et al. | |
| 2009/0270735 | A1* | 10/2009 | Cerofolini | B06B 1/0622 600/459 |
| 2010/0125199 | A1 | 5/2010 | Joo et al. | |
| 2012/0116225 | A1 | 5/2012 | Kim | |
| 2013/0218012 | A1* | 8/2013 | Specht | A61B 8/485 600/438 |
| 2014/0046173 | A1 | 2/2014 | Greenleaf et al. | |
| 2014/0046183 | A1 | 2/2014 | Park et al. | |
| 2014/0187940 | A1 | 7/2014 | Kong et al. | |
| 2014/0276069 | A1* | 9/2014 | Amble | A61B 8/5207 600/447 |
| 2015/0148673 | A1 | 5/2015 | Yoshikawa et al. | |
| 2015/0216507 | A1 | 8/2015 | Greenleaf et al. | |

FOREIGN PATENT DOCUMENTS

| | | |
|---|---|---|
| KR | 10-2010-0055743 A | 5/2010 |
| KR | 10-1068039 B1 | 9/2011 |
| KR | 10-1117550 B1 | 3/2012 |
| KR | 10-2014-0020486 A | 2/2014 |
| KR | 10-2014-0086626 A | 7/2014 |
| WO | 2009/031079 A2 | 3/2009 |
| WO | 2014/055973 A1 | 4/2014 |
| WO | 2014/103642 A1 | 7/2014 |

OTHER PUBLICATIONS

Search Report dated Jun. 29, 2015, issued by the International Searching Authority in counterpart International Patent Application No. PCT/KR2014/012781 (PCT/ISA/210).

Written Opinion dated Jun. 29, 2015, issued by the International Searching Authority in counterpart International Patent Application No. PCT/KR2014/012781 (PCT/ISA/237).

Communication dated May 31, 2016, issued by the Korean Intellectual Property Office in corresponding Korean Application No. 10-2014-0130328.

Communication dated Nov. 7, 2017, from the European Patent Office in counterpart European Application No. 14903146.0.

Mark L. Palmeri et al., "Dependence of shear wave spectral content on acoustic radiation force excitation duration and spatial beamwidth", 2014 IEEE International Ultrasonics Symposium Proceedings, (2014), (pp. 1105-1108), 10.1109/ULTSYM.2014.0271, XP32666795.

Pengfei Song et al., "Fast Shear Compounding Using Robust 2-D Shear Wave Speed Calculation and Multi-Directional Filtering", Original Contribution, 2014 World Federation for Ultrasound in Medicine & Biology, Elsevier, vol. 40, No. 6, (2014), (pp. 1343-1355), Http://dx.doi.org/10.1016/j.ultrasmedbio.2013.12.026, XP55185962.

* cited by examiner

1011

METHOD AND MEDICAL IMAGING APPARATUS FOR GENERATING ELASTIC IMAGE BY USING CURVED ARRAY PROBE

CROSS-REFERENCE TO RELATED APPLICATIONS

This application is a Continuation application of International Application PCT/KR2014/012781, filed Dec. 24, 2014, which claims priority from Korean Patent Application No. 10-2014-0130328, filed on Sep. 29, 2014, in the Korean Intellectual Property Office, the disclosures of which are incorporated herein in their entireties by reference.

BACKGROUND

1. Field

One or more exemplary embodiments relate to ultrasound medical imaging, and more particularly, to providing an elastic image by using a curved array probe.

2. Description of the Related Art

Ultrasound diagnostic apparatuses are used to non-invasively observe and diagnose the human body, by transmitting ultrasound signals generated by a probe and receiving echo signals reflected from the object, thereby obtaining images of the object. Particularly, an ultrasound diagnostic apparatus may display information regarding an object in real-time. Furthermore, there is no risk of radioactivity exposure using an ultrasound diagnostic apparatus, unlike in the use of an X-ray diagnostic apparatus, and thus, the ultrasound diagnostic apparatus is very safe. Therefore, an ultrasound diagnostic apparatus is widely used along with other types of imaging diagnostic apparatuses.

Probes are classified into several different types according to their usage. For example, an ultrasound medical imaging apparatus may include at least one of a linear array probe composed of a plurality of vibrators arranged in a line, a phased probe with a plurality of vibrators that are simultaneously driven, and a convex probe with a plurality of vibrators arranged on a convex curved surface.

Since a linear array probe is mainly used for examining a narrow region of a small organ, the linear array probe is configured to generate an image within a range of shallow depths. On the other hand, a curved array probe with vibrators arranged on a curved surface, such as a convex probe, is configured to generate an image within a depth that is greater than that for a linear array probe.

When an elastic image is generated using a curved array probe, errors may occur in the elastic image due to characteristics of the curved array probe, and scan conversion is needed. Thus, a greater amount of time may be needed to acquire an elastic image when using a curved array probe compared to when using a linear array probe. Thus, there is a need for medical imaging apparatuses and methods capable of efficiently generating an elastic image by using a curved array probe adapted to acquire an image for a depth that is greater than that for a linear array probe.

SUMMARY

One or more exemplary embodiments include a method and medical imaging apparatus for efficiently generating an elastic image by using a curved array probe.

Additional aspects will be set forth in part in the description which follows and, in part, will be apparent from the description, or may be learned by practice of the presented exemplary embodiments.

According to one or more exemplary embodiments, a method of generating an ultrasound elastic image, performed by an ultrasound imaging apparatus including a curved array probe, includes: inducing a shear wave that propagates in a second direction by transmitting a first ultrasound signal in a first direction via the curved array probe, wherein the first ultrasound signal includes a push signal for applying to an object; acquiring an echo signal by transmitting a second ultrasound signal to the object and receiving the echo signal reflected by the object in response to the second ultrasound signal via the curved array probe, wherein the second ultrasound signal is a plane wave having a straight line-like waveform parallel to the second direction; and generating an elastic image of the object by using the received echo signal.

The acquiring of the echo signal may include generating the second ultrasound signal by controlling a delay for an ultrasound wave generated by each of a plurality of transducers in the curved array probe.

A focal point of the second ultrasound signal may have a focal point located between a curved surface of the curved array probe and a central point of the curved surface of the curved array probe.

The first direction may be a depth direction of the elastic image.

The second direction may be perpendicular to the first direction.

The generating of the elastic image of the object may include beamforming the received echo signal based on a rectangular scan format.

The generating of the elastic image may further include: determining a displacement of a shear wave based on the beamformed signal; and generating the elastic image based on the determined displacement.

In the determining of the displacement related to the shear wave, displacement data may be generated without performing scan conversion on the beamformed signal.

According to one or more exemplary embodiments, an ultrasound diagnostic apparatus includes: a curved array probe including a plurality of transducers arranged on a curved surface thereof; an ultrasound transceiver that induces a shear wave that propagates in a second direction by transmitting a first ultrasound signal including a push signal for applying to an object in a first direction via the curved array probe, transmits a second ultrasound signal to the object, and receives the echo signal reflected by the object in response to the second ultrasound signal via the curved array probe, wherein the second ultrasound signal is a plane wave having a straight line-like waveform parallel to the second direction; and an image processor for generating an elastic image of the object by using the received echo signal.

The ultrasound transceiver may generate the second ultrasound signal by controlling a delay for an ultrasound wave generated by each of the plurality of transducers.

A focal point of the second ultrasound signal may be located between a curved surface of the curved array probe and a central point of the curved surface of the curved array probe.

The first direction may be a depth direction of the elastic image.

The second direction may be perpendicular to the first direction.

The ultrasound transceiver may beamform the received echo signal based on a rectangular scan format.

The image processor may generate displacement data related to the shear wave, and generates the elastic image based on the displacement data.

Furthermore, the image processor may generate the displacement data without performing scan conversion on the beamformed signal.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
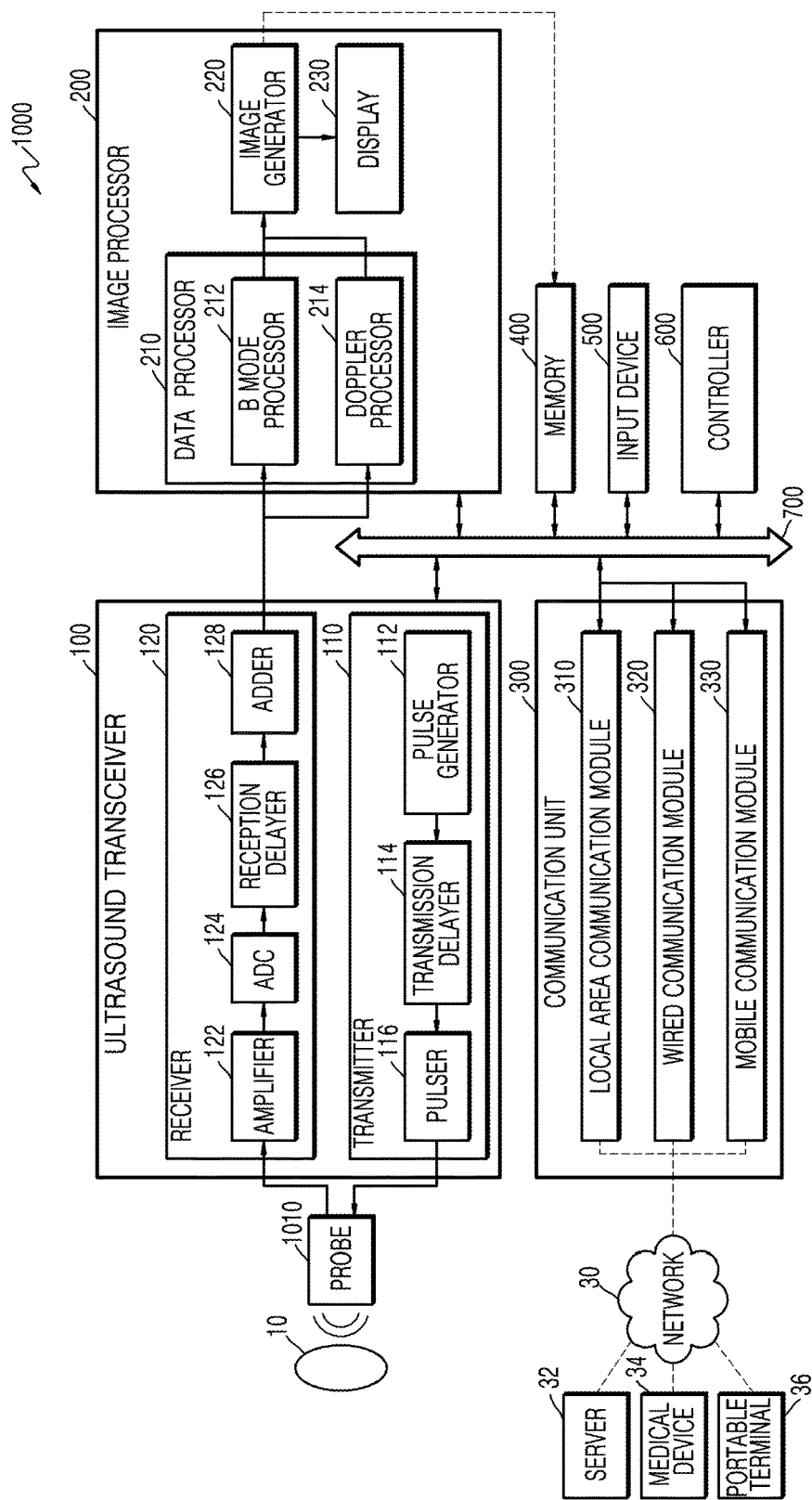
FIG. 1 is a block diagram of a configuration of an ultrasound diagnostic apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

Throughout the specification, it will also be understood that when a component "includes" or "comprises" an element, unless there is a particular description contrary thereto, it should be understood that the component can further include other elements, not excluding the other elements. In addition, terms such as " . . . unit", " . . . module", or the like refer to units that perform at least one function or operation, and the units may be implemented as hardware or software or as a combination of hardware and software.

Throughout the specification, a 'medical imaging apparatus' may be referred to as an "ultrasound diagnostic apparatus", but exemplary embodiments are not limited thereto. The medical imaging apparatus may be another medical imaging apparatus using ultrasound waves.

Throughout the specification, an "ultrasonic image" refers to an image of an object, which is obtained using an ultrasound wave. Furthermore, in the present specification, an "object" may include a person or an animal, or a part of a person or an animal. For example, the object may include the liver, the heart, the womb, the brain, a breast, the abdomen, or a blood vessel. Furthermore, the "object" may include a phantom. The phantom is a material having a volume that is approximately close to the density and effective atomic number of a living organism.

In the present specification, a "user" refers to a medical professional, such as a doctor, a nurse, a medical laboratory technologist, and a medical imaging expert, and a technician who repairs a medical apparatus, but the user is not limited thereto.

Furthermore, throughout the specification, a "shear wave" refers to an acoustic wave propagating in an elastic medium.

FIG. 1 is a block diagram of a configuration of an ultrasound diagnostic apparatus 1000 according to an exemplary embodiment. Referring to FIG. 1, the ultrasound diagnostic apparatus 1000 according to the present exemplary embodiment includes one or more probes 1010, an ultrasound transceiver 100, an image processor 200, a communication unit 300, a memory 400, an input device 500, and a controller 600, which may be connected to one another via a bus or buses 700.

The ultrasound diagnostic apparatus 1000 may be embodied as a cart type device and/or a portable device. Examples of portable ultrasound diagnostic apparatuses may include a Picture Archiving and Communications System (PACS) viewer, a smartphone, a laptop computer, a personal digital assistant (PDA), and a tablet personal computer (PC). However, exemplary embodiments are not limited thereto.

The probe 1010 transmits ultrasound signals to an object 10, based on a driving signal applied by the ultrasound transceiver 100, and receives echo signals reflected from the object 10. The probe 1010 includes a plurality of transducers that oscillate based on electric signals transmitted thereto and generate acoustic energy, that is, ultrasound waves. The probe 1010 may be connected to a main body of the ultrasound diagnostic apparatus 1000 by wire or wirelessly. In one or more exemplary embodiments, the probe 1010 may be a curved array probe composed of a plurality of transducers that are arranged on a curved surface in an array and generate ultrasound waves. For example, the array may include N×M transducers, with N being equal to or greater than 1 and M being equal to or greater than 2.

A transmitter 110 supplies a driving signal to the probe 1010 and includes a pulse generator 112, a transmission delayer 114, and a pulser 116. The pulse generator 112 generates pulses for forming transmission ultrasound waves based on a predetermined pulse repetition frequency (PRF), and the transmission delayer 114 applies a delay time for determining transmission directionality to the pulses. Pulses, to which a delay time is applied, correspond to a plurality of piezoelectric vibrators included in the probe 1010, respectively. The pulser 116 applies a driving signal (or a driving pulse) to the probe 1010 at a timing corresponding to each pulse to which a delay time is applied.

A receiver 120 generates ultrasound data by processing echo signals received from the probe 1010. The receiver 120 may include an amplifier 122, an analog-to-digital converter (ADC) 124, a reception delayer 126, and an adder 128. The amplifier 122 amplifies echo signals in each channel, and the ADC 124 performs analog-to-digital conversion on the amplified echo signals. The reception delayer 126 applies delay times for determining reception directionality to the echo signals subjected to the analog-to-digital conversion, and the adder 128 generates ultrasound data by summing the echo signals processed by the reception delayer 126. According to exemplary embodiments, the receiver 120 may omit the amplifier 122. For example, if the sensitivity of the probe 1010 or the capability of the ADC 124 to process bits is enhanced, the amplifier 122 may be omitted.

The image processor 200 generates an ultrasound image by processing ultrasound data generated by the ultrasound transceiver 100 and displays the ultrasound image. In addition, an ultrasound image may include not only a gray-scale ultrasound image obtained by scanning an object in an amplitude (A) mode, a brightness (B) mode, and a motion (M) mode, but also a Doppler image representing a moving object by using a Doppler effect. The Doppler image may include a blood flow Doppler image (also called a color Doppler image) showing a flow of blood, a tissue Doppler image showing movement of tissue, and a spectral Doppler image showing the speed at which an object moves as a waveform.

A B mode processor 212 extracts B mode components from ultrasound data and processes the B mode components. An image generator 220 may generate an ultrasound image in which signal intensities are represented as brightness based on the extracted B mode components.

Similarly, a Doppler processor 214 may extract Doppler components from ultrasound data, and the image generator 220 may generate a Doppler image indicating movement of an object as colors or waveforms based on the extracted Doppler components.

In one exemplary embodiment, the image generator 220 may generate a three-dimensional (3D) ultrasound image via volume-rendering of volume data and an elasticity image which visualizes the degree of deformation of the object 10 due to pressure. The image generator 220 may display various additional information in an ultrasound image by using text and graphics. In addition, the generated ultrasound image may be stored in the memory 400.

One or more displays 230 displays and outputs the generated ultrasound image. The display 230 may display and output not only an ultrasound image but also various information processed by the ultrasound diagnostic apparatus 1000 on a screen via a graphical user interface (GUI).

The communication unit 300 is connected to a network 30 by wire or wirelessly and communicates with an external device or server. The communication unit 300 may exchange data with a hospital server or another medical device in a hospital that is connected via a Picture Archiving and Communications System (PACS). The communication unit 300 may perform data communication according to the Digital Imaging and Communications in Medicine (DICOM) standard.

The communication unit 300 may transmit or receive data related to diagnosis of the object 10, e.g., an ultrasound image, ultrasound data, and Doppler data of the object 10, via the network 30. The communication unit 300 may also transmit or receive medical images obtained by other medical devices such as a computed tomography (CT) apparatus, a medical resonance imaging (MRI) apparatus, and an X-ray apparatus. The communication unit 300 may receive information related to a diagnosis history or a treatment schedule of a patient from a server and utilize the information to diagnose the patient, i.e., the object 10. The communication unit 300 may perform data communication with a server or a medical device in a hospital as well as a portable terminal of a doctor or a patient.

The communication unit 300 is connected to the network 30 in a wired or wireless manner and may exchange data with a server 32, a medical device 34, and/or a portable terminal 36. The communication unit 300 may include at least one component that enables communication with an external device, e.g., short-range communication module 310, a wired communication module 320, and a mobile communication module 330.

The short-range communication module 310 is a module for performing short-range communication with a device that is within a predetermined distance. Examples of short-range communication technology include a wireless Local Area Network (LAN), Wi-Fi, Bluetooth, ZigBee, Wi-Fi Direct (WFD), Ultra Wideband (UWB), Infrared Data Association (IrDA), Bluetooth Low Energy (BLE), and Near Field Communication (NFC), but this is not limiting.

The wired communication module 320 is a module for performing communication by using an electric signal or an optical signal. Examples of wired communication technology include wired communication technologies using a pair cable, a coaxial cable, an optical fiber cable, and an Ethernet cable.

The mobile communication module 330 transmits or receives wireless signals to or from at least one of a base station, an external terminal, and a server on a mobile communication network. Here, the wireless signals may include voice call signals, video call signals, or various types of data for transmission and reception of text/multimedia messages.

The memory 400 stores various data processed by the ultrasound diagnostic apparatus 1000. For example, the memory 400 may store medical data related to the diagnosis of the object 10, such as ultrasound data and ultrasound images that are input or output, and algorithms or programs that are executed in the ultrasound diagnostic apparatus 1000

The memory 400 may be embodied as any of various storage media such as a flash memory, a hard disk drive, and Electrically Erasable Programmable Read-Only Memory (EEPROM). The ultrasound diagnostic apparatus 1000 may utilize web storage or a cloud server that functions as the memory 400 online.

The input device 500 is a device via which a user inputs data for controlling the ultrasound diagnostic apparatus 1000. The input device 500 may include hardware components, such as a keypad, a mouse, a touch panel, a touch screen, a trackball, and a jog switch. However, exemplary embodiments are not limited thereto, and the input device 500 may further include various other input elements such as an electrocardiogram device, a respiration tracking device, a voice recognition sensor, a gesture recognition sensor, a fingerprint recognition sensor, an iris recognition sensor, a depth sensor, a distance sensor, etc.

The controller 600 may control operations of the ultrasound diagnostic apparatus 100. For example, the controller 600 may control operations of the probe 1010, the ultrasound transceiver 100, the image processor 200, the communication unit 300, the memory 400, and/or the input device 500.

At least one of the probe 1010, the ultrasound transceiver 100, the image processor 200, the communication unit 300, the memory 400, the input device 500, and the controller 600 may be implemented as software modules. However, exemplary embodiments are not limited thereto, and some of the above components may be implemented as hardware modules. Furthermore, at least one of the ultrasound transceiver 100, the image processor 200, and the communication unit 300 may be included in the controller 600, but exemplary embodiments are not limited thereto.

Figure 2:
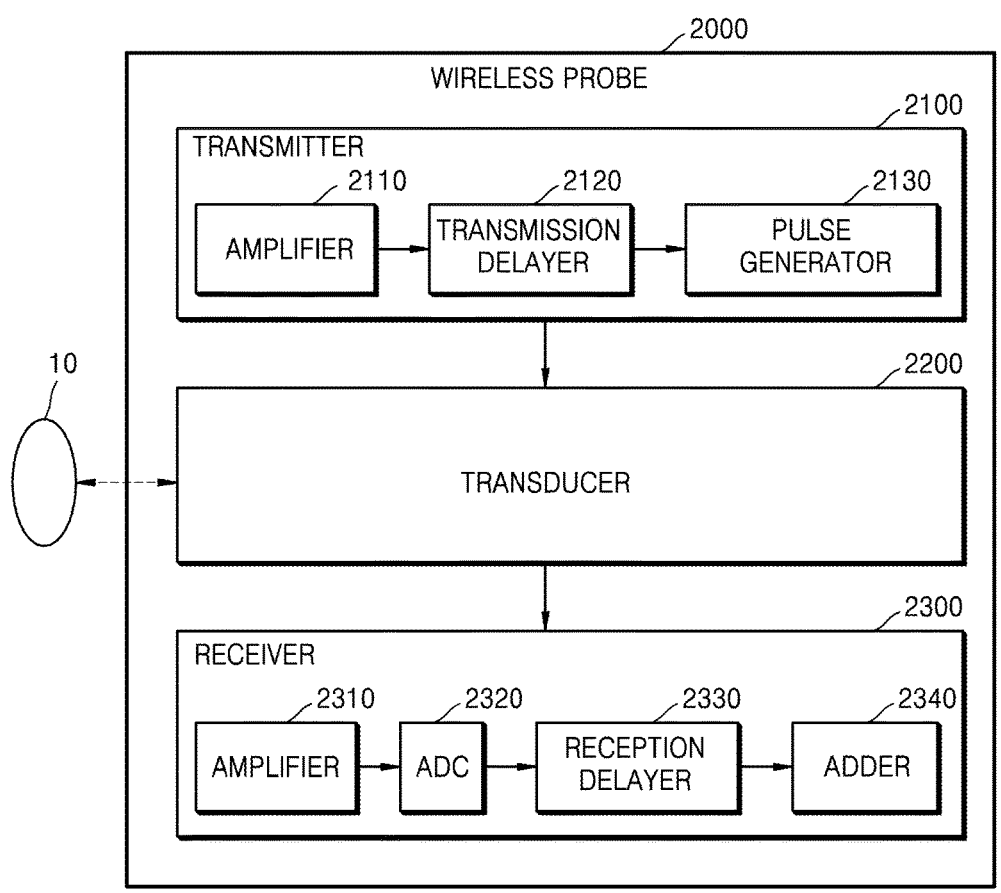
FIG. 2 is a block diagram of a configuration of a wireless probe according to an exemplary embodiment.

FIG. 2 is a block diagram of a configuration of a wireless probe 2000 according to an exemplary embodiment. Referring to FIG. 2, the wireless probe 2000 includes a plurality of transducers as described above with reference to FIG. 1 and may include some or all of the components in the ultrasound transceiver 100 according to exemplary embodiments.

The wireless probe 2000 according to the present exemplary embodiment includes a transmitter 2100, a transducer 2200, and a receiver 2300. The same descriptions as already presented with respect to FIG. 1 are omitted. According to exemplary embodiments, the wireless probe 2000 may selectively include a reception delayer 2330 and an adder 2340.

The wireless probe 2000 may transmit ultrasound signals to an object 10, receive an echo signal, generate ultrasound data, and transmit the ultrasound data wirelessly to the ultrasound diagnostic apparatus 1000 of FIG. 1.

Figure 3A:
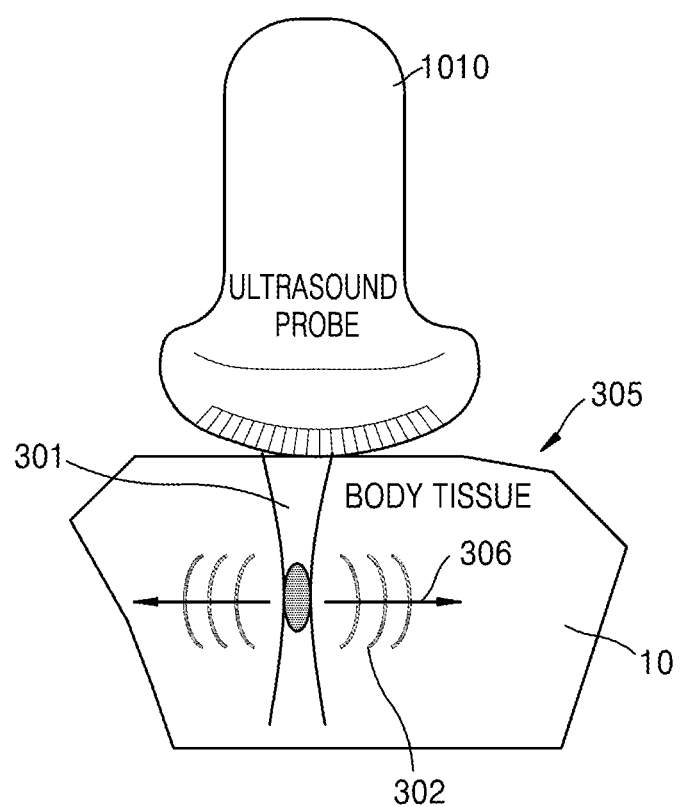
FIGS. 3A and 3B are diagrams for explaining a shear wave generated within an object.
Figure 3B:
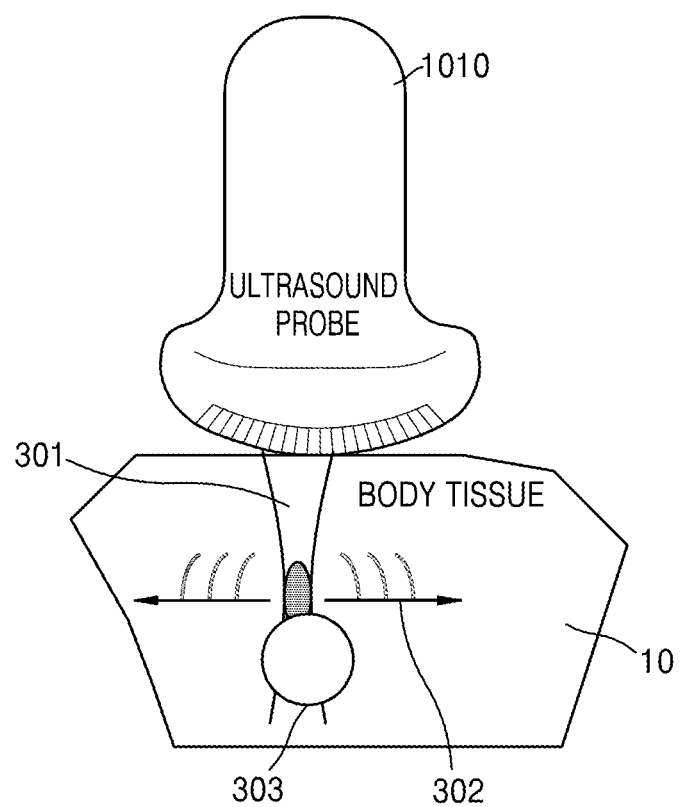

FIGS. 3A and 3B are diagrams for explaining a shear wave generated within an object 10.

Referring to FIG. 3A, the ultrasound diagnostic apparatus 1000 may transmit a push signal, e.g., a first ultrasound signal, to a region of the object 10. For example, the ultrasound diagnostic apparatus 1000 may transmit a first ultrasound signal 301 having a long wavelength through some channels (e.g., 32 to 40 channels) of the probe 1010. In some exemplary embodiments, the ultrasound diagnostic apparatus 1000 may transmit the focused first ultrasound signal 301 to a region of the object 10.

In this case, a shear wave 302 is generated in the object 10 by using the first ultrasound signal 301. For example, the shear wave 302 may propagate into a region pushed by the first ultrasound signal 301. The shear wave 302 may have a velocity of about 1 to about 10 m/s. Since the velocity (e.g., 1 to 10 m/s) of propagation of the shear wave 302 is much less than an average velocity (i.e., 1,540 m/s) of an ultrasound signal propagating in the object 10, the ultrasound diagnostic apparatus 1000 may track the shear wave 302 by using a second ultrasound signal. For example, by transmitting a tracking ultrasound signal in a direction that the shear wave 302 travels, the ultrasound diagnostic apparatus 1000 may track the velocity of the shear wave 302. A tracking ultrasound signal may have a shorter wavelength than the first ultrasound signal 301.

The shear wave 302 is induced in a direction perpendicular to the direction of the propagation of the focused first ultrasound signal 301 and is induced in a region of the object 10 substantially different from a region where the focused first ultrasound signal 301 propagates.

As shown in FIG. 3B, the first ultrasound signal 301 does not penetrate a hard tissue such as a cyst 303 or bone. For example, if the probe 1010 transmits the first ultrasound signal 301 to a region having the cyst 303, an inaccurate elastic image of the object 10 may be generated since the shear wave 302 is not generated as intended.

Figure 4:
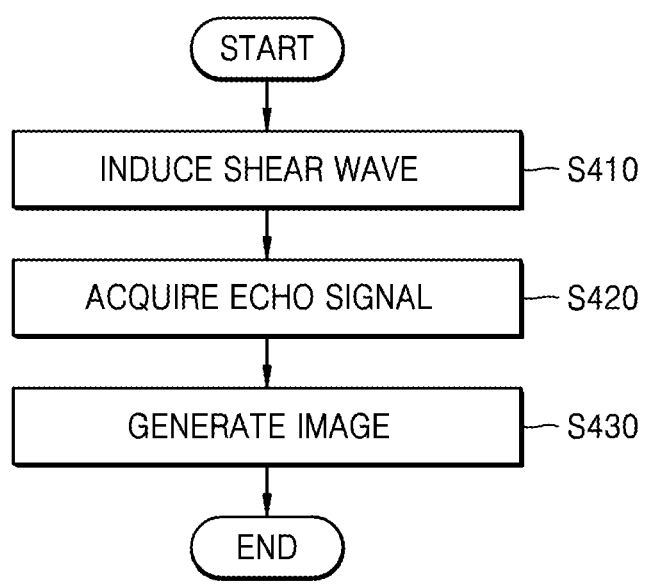
FIG. 4 is a flowchart of a process of generating an elastic image according to an exemplary embodiment.

FIG. 4 is a flowchart of a process of generating an elastic image according to an exemplary embodiment.

Referring to FIG. 4, the ultrasound diagnostic apparatus 1000 may transmit a first ultrasound signal for pushing an object to the object in a first direction 305 (operation S410). The first ultrasound signal may be a focused ultrasound signal having a long wavelength. For example, the first ultrasound signal may be a long pulse consisting of about 100 to about 800 cycles, and may be transmitted several times to a position where the long pulse will induce a shear wave. A shear wave may be induced with respect to the first direction in which the first ultrasound signal is transmitted to the object. The shear wave may propagate in two directions, e.g., a second direction 306 and a direction opposite thereto, that are perpendicular to the direction of the propagation of the first ultrasound signal. The shear wave may travel at a velocity of 1 to 10 m/s.

The ultrasound diagnostic apparatus 1000 may determine the first direction 305 by steering the first ultrasound signal generated by the probe 1010. According to an exemplary embodiment, the first direction may be an axial direction of the probe 1010. The axial direction of the probe 1010 may correspond to a depth direction of an elastic image.

If the position of the probe 1010 is fixed, the first ultrasound signal may be transmitted from a single position, or sequentially from a plurality of positions within the probe 1010. For example, according to an exemplary embodiment, there may be a single or plurality of pushed regions within the object.

For example, the ultrasound diagnostic apparatus 1000 may generate a first shear wave by transmitting a first ultrasound signal to an object by using a first channel group in the probe 1010. The ultrasound diagnostic apparatus 1000 may generate first and second shear waves by transmitting the first ultrasound signal a plurality of times by sequentially using first and second channel groups in the probe 1010.

The ultrasound diagnostic apparatus 1000 may transmit a second ultrasound signal that tracks a shear wave by using the probe 1010 (operation S420). For example, the ultrasound diagnostic apparatus 1000 may transmit a second ultrasound signal to a region of the object into which the shear wave propagates. In exemplary embodiments, the second ultrasound signal may be transmitted to the object via all of the channels in the probe 1010. Thereafter, the ultrasound diagnostic apparatus 1000 may acquire an echo signal by receiving the echo signal to the second ultrasound signal from the object. The image processor 200 of the ultrasound diagnostic apparatus 1000 may generate an elastic image (operation S430).

For example, a shear wave induced in operation S410 may be observed at 5000 to 12,000 key frames per second (kFPS) about 80 to 160 times. For example, for fast observation, a plane wave may be transmitted instead of using a focused ultrasound transmission signal that is used in a B-mode image. A beamforming process may be performed to transform channel radio frequency (RF) data acquired from an echo signal received after transmission of a plane wave into beamformed RF data or in-phase quadrature (IQ) data. The beamformed RF data or IQ data may then be transformed into displacement data.

In general, when a curved array probe is used, a beamforming process is performed based on a curved scan format in which scan lines are aligned along a curved surface where elements for generating ultrasound waves are arranged. However, in a curved scan format, an interval between adjacent scan lines is not uniform. Furthermore, as a depth of an image increases, an interval between adjacent scan lines at positions corresponding to a position of the image increases. Thus, when an elastic image is generated, a calculation is performed in consideration of the interval between scan lines. In related art, when a curved scan format is used, scan conversion needs to be performed in order to make an interval between scan lines uniform before an elastic image is generated. However, according to an exemplary embodiment, a beamforming process may be performed based on a rectangular scan format in which an interval between adjacent scan lines is uniform. Thus, the ultrasound diagnostic apparatus 1000 may generate an elastic image without performing scan conversion. To perform a beamforming process based on a rectangular scan format, the ultrasound diagnostic apparatus 1000 may use a plane wave that has a linear waveform parallel to the second direction and propagates in the first direction as the second ultrasound signal.

Figure 5:
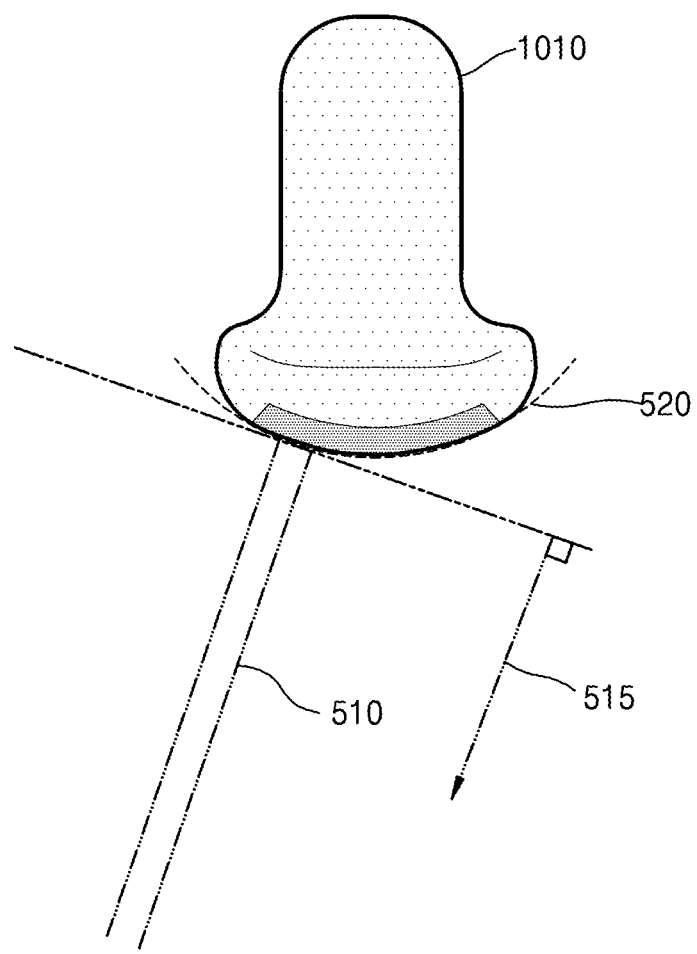
FIG. 5 is an exemplary diagram for explaining a direction in which a first ultrasound signal inducing a shear wave is transmitted using a curved array probe, according to an exemplary embodiment.

FIG. 5 is an exemplary diagram for explaining a direction in which a first ultrasound signal 510 inducing a shear wave is transmitted using a curved array probe 1010, according to an exemplary embodiment.

In general, when transducers for generating ultrasound waves are arranged along a curved surface 520 of the curved array, the first ultrasound signal 510 may be transmitted in a direction that the transducers are arranged.

Referring to FIG. 5, the first ultrasound signal 510 may be transmitted in a direction 515 that is normal to a plane tangent to the curved surface 520 along which the transducers are arranged.

Figure 6:
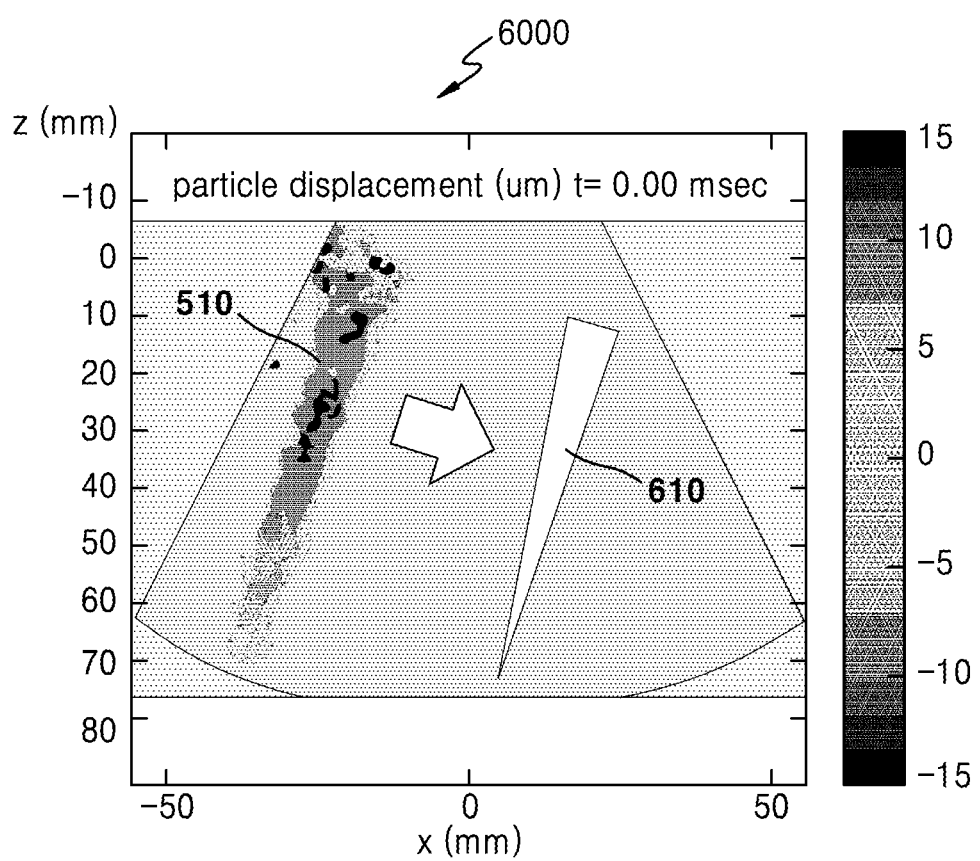
FIG. 6 is an exemplary diagram for explaining positions of a first ultrasound signal and an induced shear wave within displacement data according to the exemplary embodiment shown in FIG. 5.

FIG. 6 is an exemplary diagram for explaining positions of the first ultrasound signal 510 and a shear wave 610 induced by the first ultrasound signal 510 within displacement data 6000 according to the exemplary embodiment shown in FIG. 5.

Referring to FIG. 6, when the curved array probe 1010 transmits the first ultrasound signal 510 in the direction 515 as shown FIG. 5, a direction of transmission of the first ultrasound signal 510 within the displacement data 6000 may be oblique to a depth direction. A method of transmitting an ultrasound signal for pushing an object as shown in FIG. 6 may be referred to as a natural angle push method. In this case, a shear wave 610 is induced in a direction that is parallel to the direction of transmission of the first ultrasound signal 510 and propagates in a direction that is perpendicular to the transmission direction. Thus, the shear wave 610 is also induced in a direction oblique to the depth direction as shown in FIG. 6.

If an elastic image is generated by performing a beamforming process in a rectangular scan format, a depth direction of the elastic image does not coincide with the direction of the induced shear wave 610 since the elastic image is generated based on the displacement data 6000. To perform a beamforming process in a rectangular scan format and generate an elastic image, the depth direction of the elastic image may be made equal to the direction of the induced shear wave 610. Thus, an ultrasound signal for pushing an object may be transmitted as shown in FIG. 7.

Figure 7:
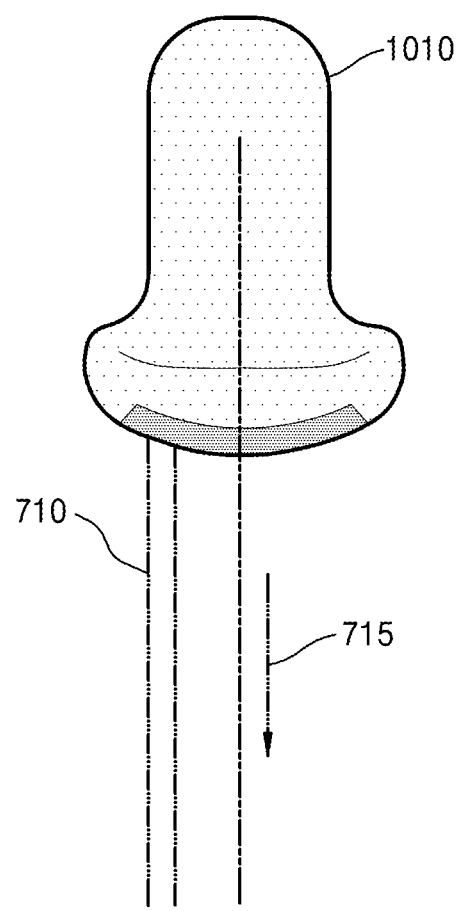
FIG. 7 is an exemplary diagram for explaining a direction in which a first ultrasound signal inducing a shear wave is transmitted using a curved array probe, according to another exemplary embodiment.

FIG. 7 is an exemplary diagram for explaining a direction in which a first ultrasound signal 710 inducing a shear wave is transmitted using a curved array probe 1010, according to another exemplary embodiment.

To make the depth direction of an elastic image coincide with the direction of an induced shear wave, the ultrasound diagnostic apparatus 1000 may transmit the first ultrasound signal 710 in an axial direction 715 of the curved array probe 1010. To do so, elements for generating the first ultrasound signal 710 may be configured to steer the direction of transmission of the first ultrasound signal 710.

Figure 8:
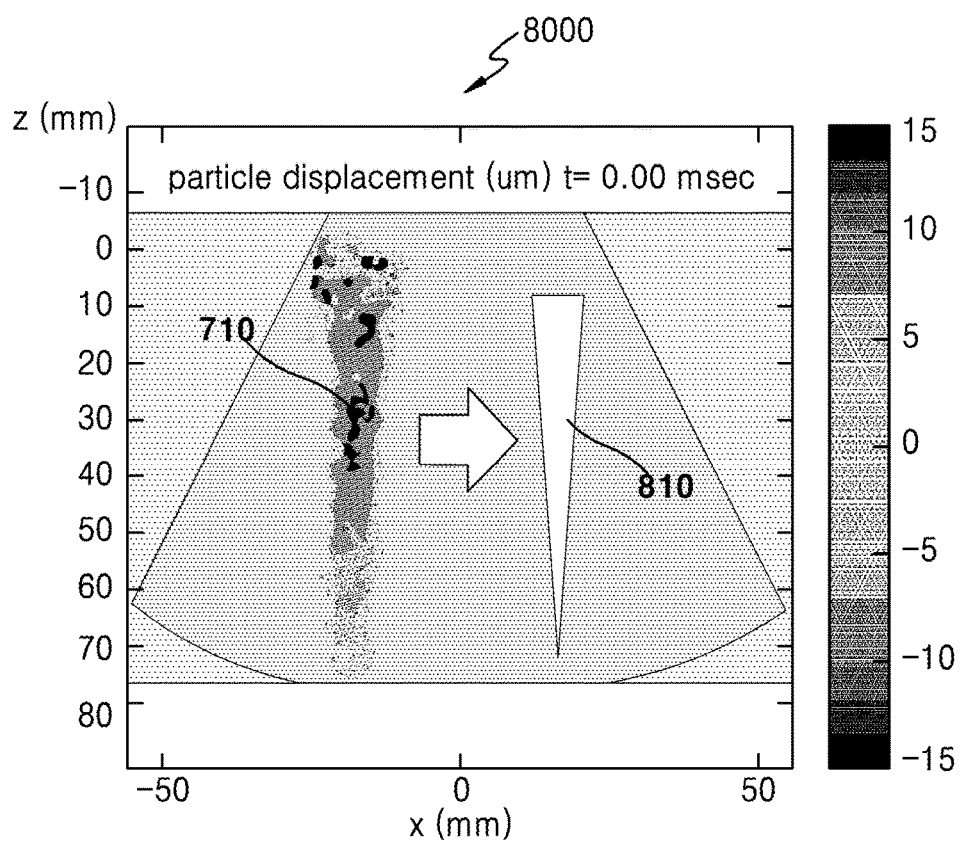
FIG. 8 is an exemplary diagram for explaining positions of a first ultrasound signal and an induced shear wave within displacement data according to the exemplary embodiment shown in FIG. 7.

FIG. 8 is an exemplary diagram for explaining positions of the first ultrasound signal 710 and a shear wave 810 induced by the first ultrasound signal 710 within displacement data 8000 according to the exemplary embodiment shown in FIG. 7.

In this case, the axial direction 715 of the curved array probe 1010 may correspond to a depth direction within the displacement data 8000. Furthermore, since an elastic image is generated based on the displacement data 8000, the axial direction 715 of the curved array probe 1010 may correspond to a depth direction of the elastic image. If the curved array probe 1010 transmits the first ultrasound signal 710 in the axial direction 715 of the probe 1010 as shown in FIG. 7, the shear wave 810 is induced in a depth direction of an image as shown in FIG. 8. A method of transmitting an ultrasound signal for pushing an object may be referred to as a vertical push method.

When the first ultrasound signal 710 is transmitted as shown in FIGS. 7 and 8, a direction in which the shear wave 810 is observed may be made substantially the same as a direction of the induced shear wave 810. By making the direction of observation of the shear wave 810 coincide with the direction of the induced shear wave 810, the ultrasound diagnostic apparatus 1000 of an exemplary embodiment may generate a more accurate elastic image than an ultrasound diagnostic apparatus of the related art.

Figure 9:
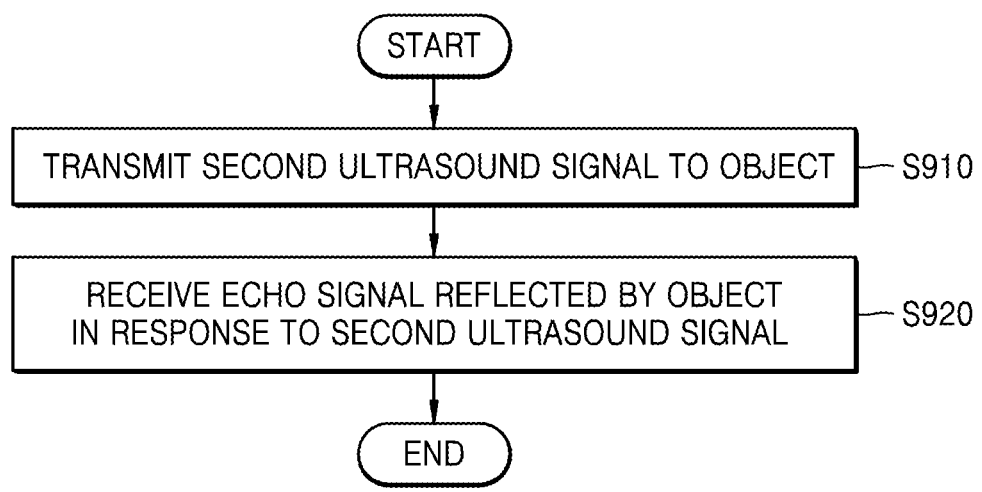
FIG. 9 is a flowchart of a process of acquiring an echo signal in a medical imaging apparatus, according to an exemplary embodiment.

FIG. 9 is a flowchart of a process of acquiring an echo signal in the ultrasound diagnostic apparatus 1000, according to an exemplary embodiment.

Referring to FIGS. 4 and 9, during operation S420 shown in FIG. 4, the ultrasound diagnostic apparatus 1000 may transmit the second ultrasound signal for observing the shear wave induced in operation S410 to the object (operation S910). According to exemplary embodiments, the second ultrasound signal may be a straight plane wave having a straight line-like waveform parallel to the second direction 306 that is the direction of propagation of the shear wave that is induced by the first ultrasound signal transmitted in the first direction. For example, the ultrasound diagnostic apparatus 1000 may make the direction of the induced shear wave coincide with the direction in which the shear wave is observed. The ultrasound diagnostic apparatus 1000 may generate a plane wave by controlling a delay for an ultrasound wave generated by each of a plurality of transducers in the probe 1010, as described in more detail below with reference to FIGS. 12 and 13.

Subsequently, the ultrasound diagnostic apparatus 1000 may receive an echo signal reflected from the object to which the second ultrasound signal is transmitted (operation S920). In this case, the echo signal may be received in the same direction that the second ultrasound signal is transmitted.

Figure 10A:
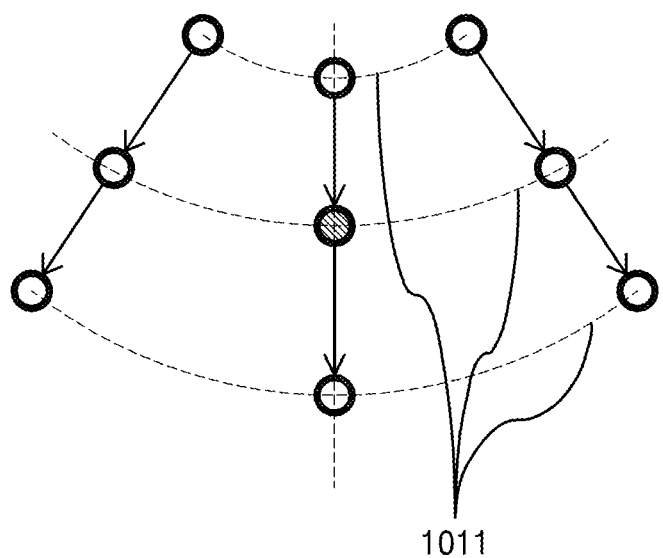
FIGS. 10A and 10B are conceptual diagrams for explaining a waveform of a second ultrasound signal transmitted from a probe.
Figure 10B:
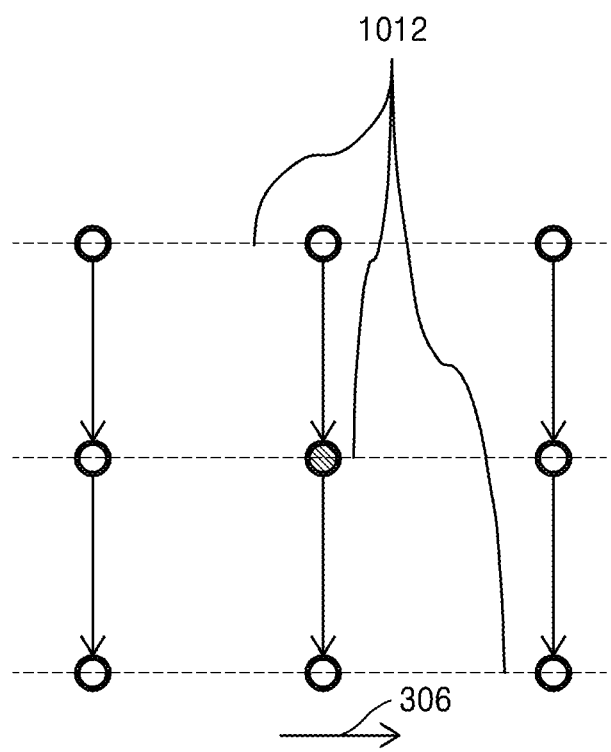
Figure 16:
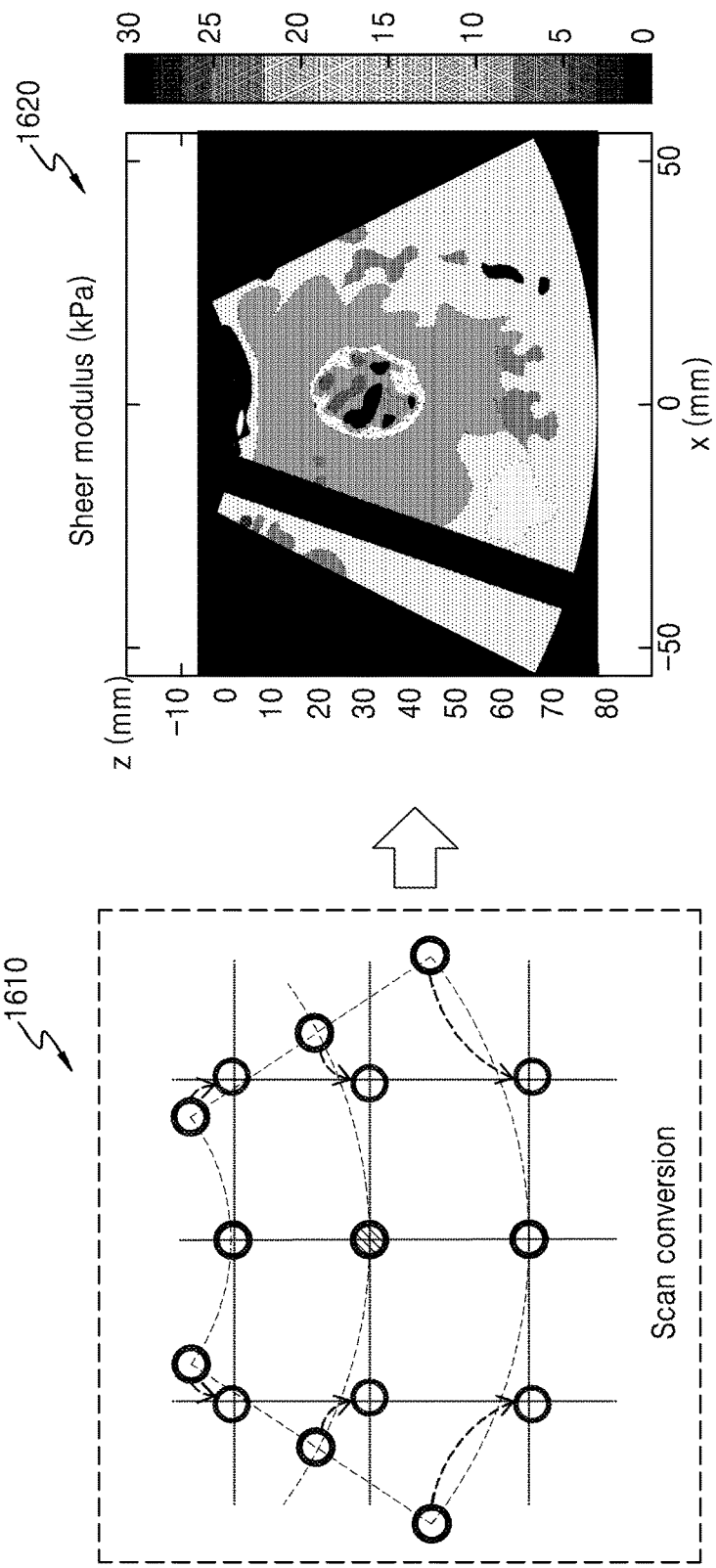
FIG. 16 is a conceptual diagram for explaining an image processing process for generating an elastic image by using scan conversion when a second ultrasound signal has a curved waveform.

FIGS. 10A and 10B are conceptual diagrams for explaining a shape of a second ultrasound signal transmitted from a probe. Referring to FIG. 10A, when an ultrasound wave for tracking a shear wave is transmitted using a curved array probe, an ultrasound wave 1011 having a waveform whose shape is substantially the same as a shape of a curved surface 520 of FIG. 5 along which elements for generating ultrasound waves are arranged is transmitted from the probe toward the object. However, in this case, an elastic image may be acquired only after performing scan conversion 1610 as shown in FIG. 16.

Referring to FIG. 10B, according to an exemplary embodiment, the ultrasound diagnostic apparatus 1000 may observe a shear wave by using a straight plane wave 1012 having a substantially straight line-like waveform parallel to the second direction 306 that is the direction of propagation of the shear wave.

Figure 11:
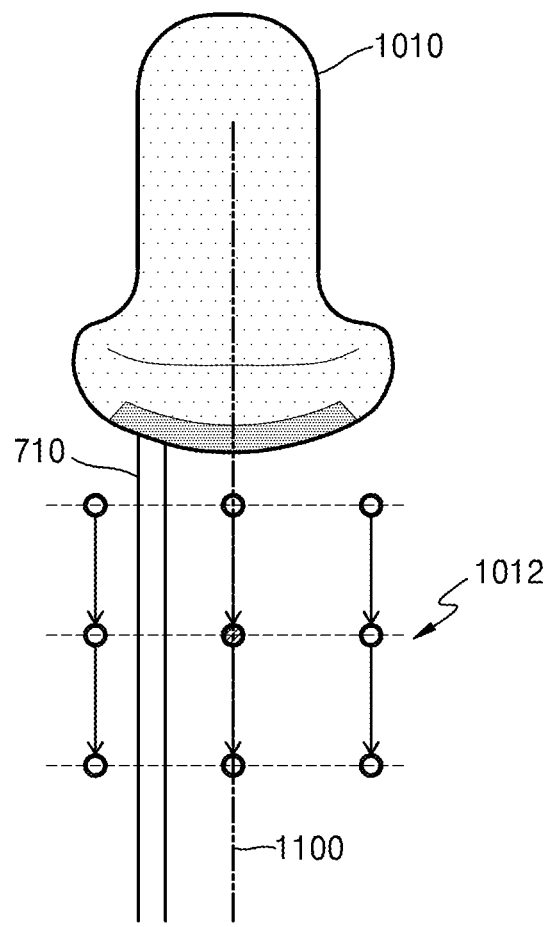
FIG. 11 is a conceptual diagram for explaining a second ultrasound signal used for tracking a shear wave induced based on the exemplary embodiment shown in FIG. 7.

FIG. 11 is a conceptual diagram for explaining a second ultrasound signal 1012 used for tracking a shear wave induced based on the exemplary embodiment shown in FIG. 7. Referring to FIG. 11, the ultrasound diagnostic apparatus 1000 may transmit the first ultrasound signal 710 according to a vertical push method by using the curved array probe 1010. After transmission of the first ultrasound signal 710, the ultrasound diagnostic apparatus 1000 may transmit the second ultrasound signal 1012 by using the probe 1010 to observe the shear wave induced by the first ultrasound signal 710.

Figure 12:
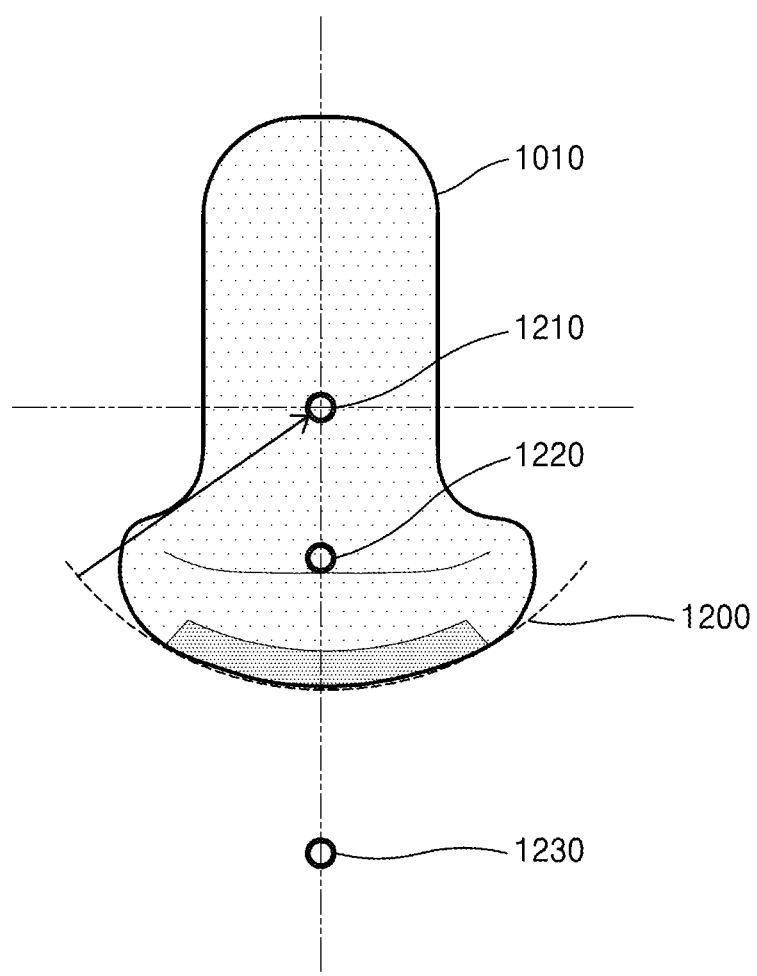
FIG. 12 is a conceptual diagram for explaining a method of generating a plane wave by using a curved array probe.

FIG. 12 is a conceptual diagram for explaining a method of generating a plane wave using a curved array probe 1010.

According to exemplary embodiments, the ultrasound diagnostic apparatus 1000 may adjust a focal point of a second ultrasound signal generated by the curved array probe 1010 by controlling a delay for each transducer in the curved array probe 1010. When the second ultrasound signal is focused at a negative position, a negative focal point 1220 may be created between a curved surface 1200 and a central point 1210 of the curved surface 1200, e.g., a center of an arc formed by the curved surface 1200, of the curved array probe 1010. Conversely, when the second ultrasound signal is focused with a positive value, a positive focal point 1230 may be formed at an opposite side of the central point 1210 with respect to the curved surface 1200. For example, if the second ultrasound signal is focused at −100%, a focal point of the second ultrasound signal may be located at the central point 1210 of the curved array probe 1010.

Figure 13:
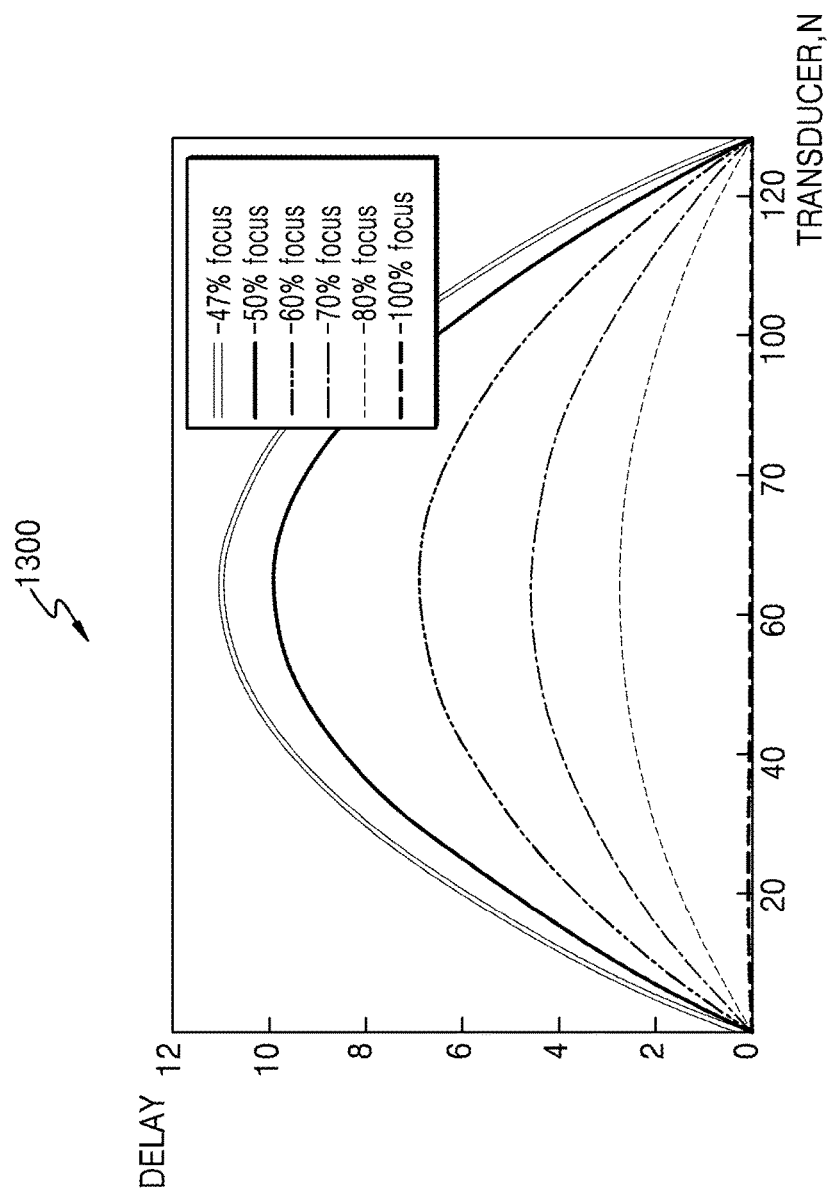
FIG. 13 is a graph showing a delay for each transducer determined according to a position of a focal point of a second ultrasound signal.

FIG. 13 is a graph 1300 showing a delay for each transducer determined to form a position of a focal point of a second ultrasound signal. The graph 1300 shows a position of a focal point that is formed by varying a delay for each transducer.

If the second ultrasound signal is experimentally focused at −47%, the second ultrasound signal may have a shape of a plane wave. However, exemplary embodiments are not limited thereto.

Figure 14:
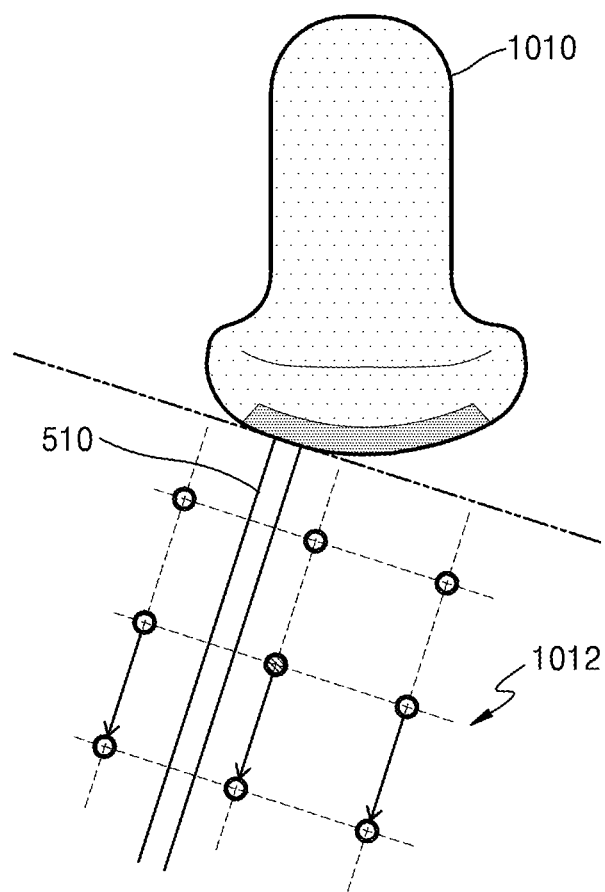
FIG. 14 is a conceptual diagram for explaining a second ultrasound signal used for tracking a shear wave induced based on the exemplary embodiment shown in FIG. 5.

FIG. 14 is a conceptual diagram for explaining a second ultrasound signal used for tracking a shear wave induced based on the exemplary embodiment shown in FIG. 5.

According to exemplary embodiments, when the first ultrasound signal 510 is transmitted from the curved array probe 1010 based on a natural angle push method, the ultrasound diagnostic apparatus 1000 may transmit a second ultrasound signal 1012 along a direction of propagation of the first ultrasound signal 510 as shown in FIG. 14.

Figure 15:
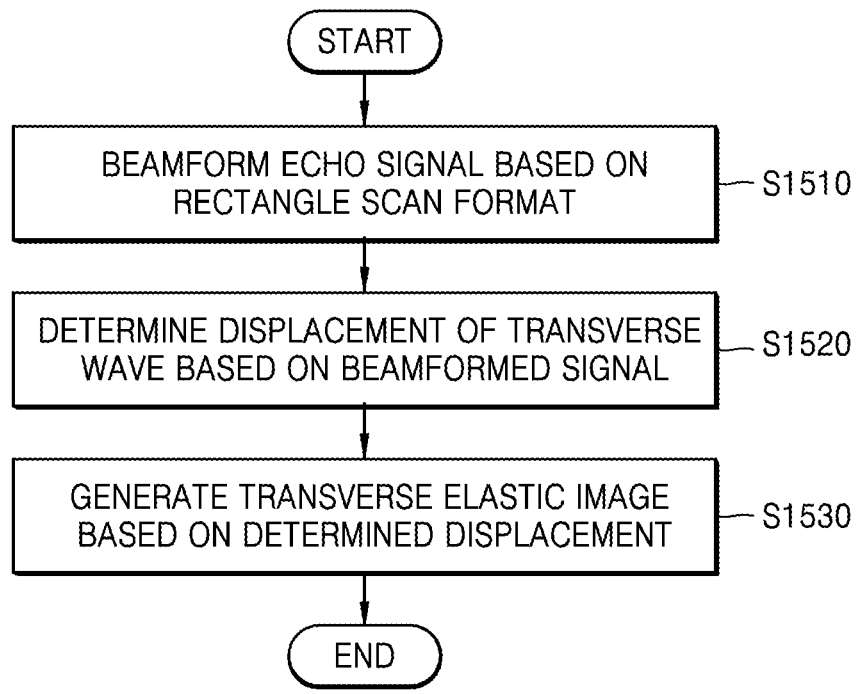
FIG. 15 is a flowchart of a process of generating an elastic image in a medical imaging apparatus, according to another exemplary embodiment.

FIG. 15 is a flowchart of a process of generating an elastic image in the ultrasound diagnostic apparatus 1000, according to another exemplary embodiment;

First, the ultrasound diagnostic apparatus 1000 may perform a beamforming process on the echo signal acquired in operation S420 shown in FIG. 4, based on a rectangular scan format (operation S1510). In the rectangular scan format, since scan lines are arranged to create a rectangular image, an interval between adjacent scan lines is uniform.

Thereafter, the ultrasound diagnostic apparatus 1000 may determine a displacement of a shear wave based on a signal beamformed using the rectangular scan format in operation S1510 without performing a scan conversion process (operation S1520). In operation S1520, the ultrasound diagnostic apparatus 1000 may also generate displacement data related to the determined displacement of the shear wave. According to one or more exemplary embodiments, displacement data related to about 80 to about 160 scenes may be generated in operation S1520.

Then, the ultrasound diagnostic apparatus 1000 may generate an elastic image based on a displacement contained in the displacement data (operation S1530). Furthermore, according to exemplary embodiments, the ultrasound diagnostic apparatus 1000 may change a position where the shear wave is induced and repeat operations S410 through S430 shown in FIG. 4, thereby generating a plurality of elastic images. Subsequently, the ultrasound diagnostic apparatus 1000 may combine the plurality of elastic images into a final elastic image.

FIG. 16 is a conceptual diagram for explaining an image processing process for generating an elastic image by using a scan conversion process when a second ultrasound signal has a curved waveform. In detail, FIG. 16 shows observation of a shear wave using the ultrasound signal 1011 having a curved waveform as shown in FIG. 10A by using the probe 1010 having transducers arranged along a curved surface.

In this case, the ultrasound diagnostic apparatus 1000 may perform scan conversion 1610 to make the gaps between scan lines between signals beamformed based on a curved scan format uniform. Then, the ultrasound diagnostic apparatus 1000 may generate a fan-shaped elastic image 1620 based on the result of the scan conversion 1610.

Figure 17:
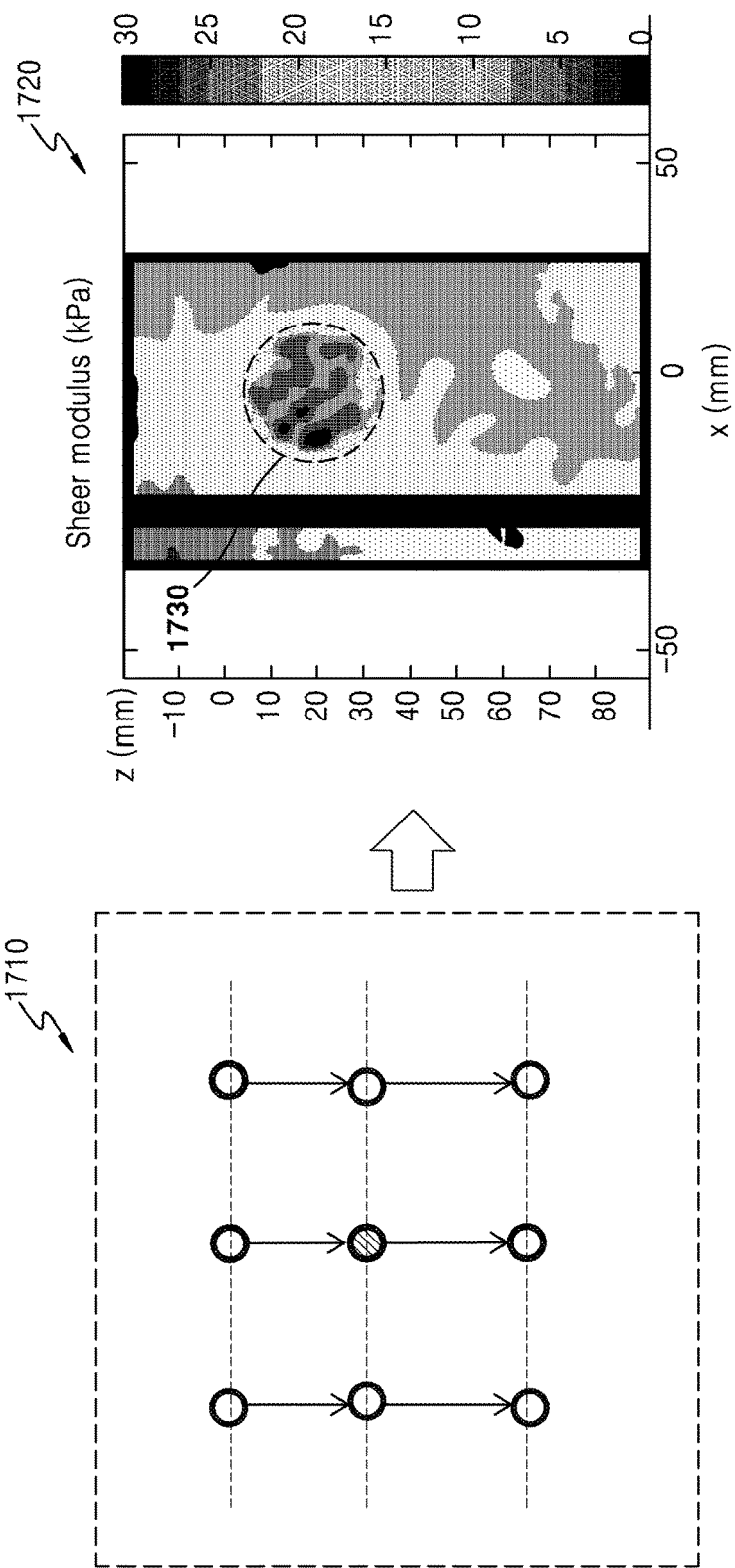
FIG. 17 is a conceptual diagram for explaining an image processing process for generating an elastic image in a medical imaging apparatus when a second ultrasound signal is a plane wave having a straight line-like waveform.

FIG. 17 is a conceptual diagram for explaining an image processing process for generating an elastic image in a medical imaging apparatus when a second ultrasound signal is a plane wave having a straight line-like waveform.

According to exemplary embodiments, the second ultrasound signal is a straight plane wave 1710. Thus, if an echo signal is beamformed using a rectangular scan format, a separate scan conversion process is not needed since an interval between scan lines is uniform.

Thus, the ultrasound diagnostic apparatus 1000 may generate a rectangular elastic image 1720 without performing a separate scan conversion process. Since an error does not occur due to a mismatch between directions of displacements, the elastic image 1720 acquired based on the rectangular scan format may be highly accurate.

Furthermore, if a directional filter is used, only a region of interest (ROI) 1730 in the elastic image 1720 may be calculated, thereby reducing the calculation.

Figure 18:
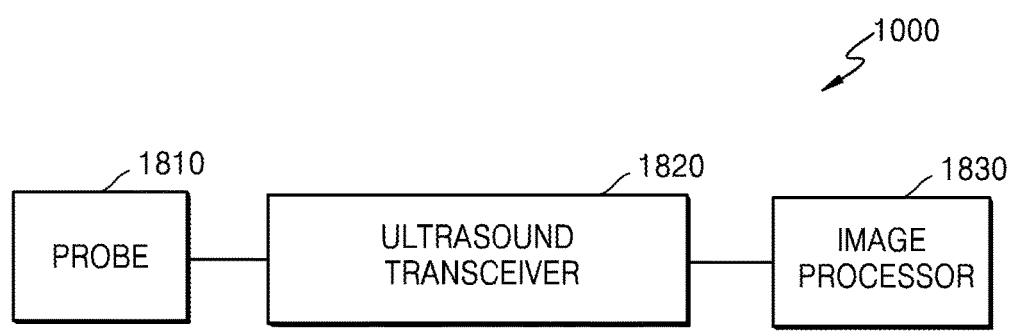
FIG. 18 is a simplified block diagram of a configuration of an ultrasound diagnostic apparatus according to an exemplary embodiment.

FIG. 18 is a simplified block diagram of a configuration of an ultrasound diagnostic apparatus 1000 according to an exemplary embodiment.

The ultrasound diagnostic apparatus 1000 according to the present exemplary embodiment may include a probe 1810, an ultrasound transceiver 1820, and an image processor 1830.

The probe 1810 may generate an ultrasound wave and receive an echo signal in response to the generated ultrasound wave. The probe 1810 may be a curved array probe having transducers for generating ultrasound waves which are arranged along a curved surface.

The ultrasound transceiver 1820 may transmit a first ultrasound signal for pushing an object in a first direction by using the probe 1810. According to exemplary embodiments, the first direction may correspond to a depth direction of an elastic image. As the first ultrasound signal is transmitted to the object, a shear wave may be induced from the object and propagate in a second direction which may be perpendicular to the first direction. The ultrasound transceiver 1830 may transmit a second ultrasound signal for observing the shear wave to the object via the probe 1810.

The second ultrasound signal may be a straight plane wave having a linear waveform parallel to the second direction. The ultrasound transceiver 1820 may transmit a plane wave to the object by controlling a delay for the second ultrasound signal so that a focal point of the second ultrasound signal is located between a curved surface of the probe 1810 that generates the second ultrasound signal and a central point of the curved surface of the probe 1810.

The ultrasound transceiver 1820 may receive an echo signal reflected from the object in response to the second ultrasound signal via the probe 1810. The ultrasound transceiver 1820 may then beamform the received echo signal based on a rectangular scan format.

The image processor 1830 may generate an elastic image of the object by using the received echo signal. In detail, the image processor 1830 may generate displacement data related to a shear wave based on a beamformed signal and generate an elastic image based on the displacement data. Particularly, since the received echo signal is beamformed based on the rectangular scan format, the image processor 1830 may generate displacement data without performing scan conversion.

As described above, according to one or more of exemplary embodiments, scan conversion is not performed when an elastic image is acquired using a curved array probe, thereby reducing the calculation time and intensity.

Furthermore, only an ROI may be calculated by applying a directional filter, thereby shortening the calculation time.

In addition, since a direction in which a transverse wave is observed coincides with a direction in which a transverse wave is induced and is fixed, it is possible to generate highly accurate elastic images.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of generating an elastic image, the method comprising:
    inducing a shear wave that propagates in a second direction by transmitting a first ultrasound signal comprising a push signal to an object in a first direction, by a curved array probe;
    transmitting, by transducers arranged on a continuously curved surface of the curved array probe, a second ultrasound signal to the object for tracking the shear wave, the second ultrasound signal being a plane wave having a wavefront as a straight line parallel to the second direction and including scan lines, all of the scan lines being disposed in parallel and equidistantly from one another and in parallel to the first direction of the first ultrasound signal;
    receiving an echo signal reflected by the object in response to the second ultrasound signal, via the curved array probe;
    beamforming the received echo signal based on a rectangular scan format in which all of the scan lines are disposed in parallel and equidistantly from one another so that distances between each two received adjacent scan lines are uniform; and
    displaying the elastic image of the object in a rectangular form by using the beamformed echo signal.

2. The method of claim 1, wherein the transmitting the second ultrasound signal comprises:
    generating the plane wave by controlling a delay for corresponding ultrasound signals generated by the transducers of the curved array probe.

3. The method of claim 2, wherein the transmitting the second ultrasound signal comprises forming the plane wave by controlling the delay of each of the transducers to focus at a negative focal point located between the continuously curved surface of the curved array probe and a central point of the continuously curved surface of the curved array probe, the central point being a point at which the negative focal point is located when the second ultrasound signal is focused at −100%.

4. The method of claim 1, wherein the first direction is a depth direction of the elastic image.

5. The method of claim 1, wherein the second direction is perpendicular to the first direction.

6. The method of claim 1, wherein the displaying the elastic image comprises:
    determining a displacement of the shear wave based on the beamformed echo signal; and
    generating the elastic image based on the displacement.

7. The method of claim 6, wherein the determining the displacement of the shear wave comprises:
    generating displacement data without performing scan conversion on the beamformed echo signal.

8. An ultrasound diagnostic apparatus comprising:
    a curved array probe including a continuously curved surface and transducers arranged on the continuously curved surface;
    an ultrasound transceiver configured to:
        induce a shear wave that propagates in a second direction by transmitting a first ultrasound signal comprising a push signal to an object in a first direction via the curved array probe,
        transmit a second ultrasound signal to the object for tracking the shear wave, the second ultrasound signal being a plane wave having a wavefront as a straight line parallel to the second direction and including scan lines, all of the scan lines being disposed in parallel and equidistantly from one another and in parallel to the first direction of the first ultrasound signal, receive an echo signal reflected by the object in response to the second ultrasound signal via the curved array probe, and beamform the received echo signal based on a rectangular scan format in which all of the scan lines are disposed in parallel and equidistantly from one another so that distances between each two received adjacent scan lines are uniform; and a display configured to display an elastic image of the object in a rectangular form by using the beamformed echo signal.

9. The ultrasound diagnostic apparatus of claim 8, wherein the ultrasound transceiver is further configured to generate the plane wave by controlling a delay for corresponding ultrasound signals generated by the transducers.

10. The ultrasound diagnostic apparatus of claim 9, wherein the ultrasound transceiver is further configured to form the plane wave by controlling the delay of each of the transducers to focus at a negative focal point located between the continuously curved surface of the curved array probe and a central point of the continuously curved surface of the curved array probe, the central point being a point at which the negative focal point is located when the second ultrasound signal is focused at −100%.

11. The ultrasound diagnostic apparatus of claim 8, wherein the first direction is a depth direction of the elastic image.

12. The ultrasound diagnostic apparatus of claim 8, wherein the second direction is perpendicular to the first direction.

13. The ultrasound diagnostic apparatus of claim 8, further comprising:

an image processor configured to generate displacement data related to the shear wave, and generate the elastic image based on the displacement data.

14. An ultrasound medical imaging apparatus comprising:
a probe including a continuously curved surface and transducers arranged on the continuously curved surface in an N×M array; and
a processor configured to perform:

controlling the transducers to transmit a first ultrasound signal to an object in a first direction, the first ultrasound signal comprising a push signal configured to induce a shear wave in the object, the shear wave propagating in a second direction perpendicular to the first direction;

controlling the transducers to transmit a second ultrasound signal to the object for tracking the shear wave, and receive an echo signal reflected by the object in response to the second ultrasound signal, the second ultrasound signal including a plane wave having a wavefront as a straight line parallel to the second direction and including scan lines, all of the scan lines being disposed in parallel and equidistantly from one another and in parallel to the first direction of the first ultrasound signal;

beamforming the received echo signal based on a rectangular scan format in which all of the scan lines are disposed in parallel and equidistantly from one another so that distances between each two received adjacent scan lines are uniform; and controlling an image processor to generate an elastic image of the object based on the received echo signal.

15. The ultrasound medical imaging apparatus of claim 14, wherein the processor is further configured to control the transducers to generate the plane wave by controlling a delay for corresponding ultrasound signals generated by the transducers.

16. The ultrasound medical imaging apparatus of claim 14, wherein the first direction is a depth direction of the elastic image.

17. The ultrasound medical imaging apparatus of claim 14, wherein the processor is further configured to generate displacement data of the shear wave, and control the image processor to generate the elastic image based on the displacement data.

18. The method of claim 1, wherein the transmitting the second ultrasound signal comprises transmitting the plane wave in the first direction, and
the wavefront of the plane wave extends in the second direction which is the same as that in which the shear wave propagates.

19. The method of claim 1, wherein a wavelength of the second ultrasound signal is shorter than that of the first ultrasound signal.

20. The method of claim 1, wherein the continuously curved surface of the curved array probe is convex with respect to the curved array probe.

* * * * *